US006842736B1

(12) United States Patent
Brzozowski

(10) Patent No.: US 6,842,736 B1
(45) Date of Patent: Jan. 11, 2005

(54) DRUG AUDITING METHOD AND SYSTEM

(76) Inventor: David J. Brzozowski, 18 Harrison Dr. Suite 7, Wolcott, CT (US) 06716

( * ) Notice: Subject to any disclaimer, the term of this patent is extended or adjusted under 35 U.S.C. 154(b) by 489 days.

(21) Appl. No.: 09/176,416

(22) Filed: Oct. 21, 1998

(51) Int. Cl.[7] ............................................. G06F 17/60
(52) U.S. Cl. ................................. 705/2; 705/3; 705/1
(58) Field of Search ................................... 705/2, 3, 1

(56) References Cited

U.S. PATENT DOCUMENTS

| | | | | |
|---|---|---|---|---|
| 4,616,316 A | * | 10/1986 | Hanpeter et al. | 221/2 |
| 4,695,954 A | * | 9/1987 | Rose et al. | 221/15 |
| 4,766,542 A | | 8/1988 | Pilarczyk | 705/3 |
| 4,847,764 A | * | 7/1989 | Halvorson | 700/231 |
| 5,014,875 A | * | 5/1991 | McLaughlin et al. | 221/2 |
| 5,047,948 A | * | 9/1991 | Turner | 700/237 |
| 5,057,677 A | * | 10/1991 | Bertagna et al. | 235/380 |
| 5,072,383 A | | 12/1991 | Brimm et al. | 705/2 |
| 5,267,174 A | * | 11/1993 | Kaufman et al. | 700/242 |
| 5,299,121 A | | 3/1994 | Brill et al. | 600/301 |
| 5,327,341 A | | 7/1994 | Whalen et al. | 705/3 |
| 5,329,459 A | * | 7/1994 | Kaufman et al. | 700/242 |
| 5,412,372 A | * | 5/1995 | Parkhurst et al. | 340/568.1 |
| 5,420,786 A | | 5/1995 | Felthauser et al. | 705/2 |
| 5,710,551 A | * | 1/1998 | Ridgeway | 340/870.09 |
| 5,732,401 A | | 3/1998 | Conway | 705/29 |
| 5,737,539 A | | 4/1998 | Edelson et al. | 705/3 |
| 5,899,998 A | * | 5/1999 | McGauley et al. | 707/104 |
| 5,945,651 A | * | 8/1999 | Chorosinski et al. | 235/375 |
| 5,991,728 A | * | 11/1999 | DeBusk et al. | 705/2 |
| 5,996,889 A | * | 12/1999 | Fuchs et al. | 235/375 |
| 6,014,631 A | * | 1/2000 | Teagarden et al. | 705/3 |

FOREIGN PATENT DOCUMENTS

JP          59231676 A   * 12/1984  ........... G06F/15/42

OTHER PUBLICATIONS

Ronna Bonstein, "OmniCell Launches a New Product for Dispesing Medications", Business Wire, p12010128, Dec. 1995.*
Antoinette Vecchio, New Products and Services .(News Briefs), Health Management Technology, 21,2,60, Dec. 1995.*

* cited by examiner

Primary Examiner—Tariq R. Hapiz
Assistant Examiner—Akiba Robinson-Boyce
(74) Attorney, Agent, or Firm—Bachman & LaPointe, P.C.

(57) ABSTRACT

The present invention relates to a system and a method for auditing drug usage within a medical care facility. The system comprises an automated drug delivery system for dispensing a plurality of drugs to medical care providers or users, which delivery system has a plurality of drug dispensing stations located throughout the medical care facility and a centralized archive for storing data. Each drug dispensing station includes a console for inputting information about each transaction involving at least one of the drugs and a link for transferring the inputted information to the centralized archive. The system further comprises a processing unit for receiving the transactional information from the centralized archive and for processing it so as to generate at least one report for a defined period of time which detects patterns and abnormalities in distribution and usage of selected ones of the drugs. The method describes the manner in which the transactional information is manipulated to detect any patterns and abnormalities in the distribution and usage of the drugs.

41 Claims, 6 Drawing Sheets

DRUG AUDITING METHOD AND SYSTEM

BACKGROUND OF THE INVENTION

The present invention relates to a system and a method for auditing the use of prescribed materials, such as drugs, medications, and narcotics, in hospitals and other medical care facilities.

The advent of computers has increased the ability of medical facilities, such as hospitals, doctor's offices, and pharmacies, to track various materials which they routinely dispense to patients/customers. The patent literature is replete with various systems capable of being used by these facilities for a variety of different purposes. For example, U.S. Pat. No. 4,766,542 to Pilarczyk illustrates a system and software for pharmaceutical prescription compliance. The system is intended to contact customers of a pharmacy automatically to remind them that their prescriptions need to be refilled. The system uses a computer, memory, and automatic telephone dialing and voice synthesizing equipment. Information concerning each customer and his or her prescription is placed in a database in the memory. A schedule file which lists customer name, phone number, the drug prescribed and refill due date is created from this information. The schedule file is kept in chronological order by refill due date. At selected times, customers whose prescriptions are due to be refilled within selected time periods are automatically contacted by the computer using the automatic telephone dialer. When the telephone is answered, the voice synthesizer identifies the customer by name, the prescribed drug and prescription number. The system generates various reports for the pharmacist concerning its automatic activities.

U.S. Pat. No. 5,072,383 to Brimm et al. relates to a hospital information system which includes a plurality of terminals having display means and data entry means. Patient information is entered into the system via the terminals, is organized hierarchically in the system, and may be displayed to users having proper access to the system. The system provides a time-oriented task list, which is automatically generated from data which has been entered from physician and nursing orders. Tasks may be chartered by a system user directly onto a system form, and the task list and any associated form(s) are automatically updated.

U.S. Pat. No. 5,299,121 to Brill et al. relates to a non-prescription drug medication screening system. The system is intended for use in pharmacies and uses customer inputs to assist the customer with the selection of an appropriate non-prescription medication to relieve symptoms of an illness, injury or the like. The system uses an expert system to perform the selection. The system also uses a personal computer with a keyboard, monitor and disk drive as input/output devices with appropriate programming for prompting a user to input information which is used by a knowledge base to determine non-prescription medications which may be purchased by the customer to relieve symptoms of injuries and illnesses covered by the knowledge base. The system operates by prompting a user to input basic customer information. After the basic customer information has been inputted, the customer is prompted to select one main symptom category from a list displayed and the choice made results in the appropriate knowledge base being loaded for the next step. The logic of the loaded knowledge base itself determines which questions are asked of the customer by the display of appropriate questions on the monitor. The output of each knowledge base on the completion of the questions and answers is a list of component medications recommended for use with the symptoms described. The list of component medications generated by the execution of the knowledge base is used to search a database to find the appropriate product to be recommended.

U.S. Pat. No. 5,327,341 to Whalen et al. is directed to a computerized file maintenance system for managing medical records including narrative reports. The file maintenance system processes multiple files of a client/patient type, the files having record sets in an organizational structure combining a plurality of standard, categorical, field-defined records with identified text fields of fixed character length with a plurality of hybrid categorical, extended-field records of virtually unlimited character length with means for editing entered text without reentry of previously entered data in the extended field.

U.S. Pat. No. 5,420,786 to Felthauser et al. describes a method of estimating product distribution. In this method, sales activity of a product at sales outlets including sales outlets at which sales activity data is sampled and unsampled sales outlets is estimated by determining the distances between each of the sampled sales outlets and each of the unsampled sales outlets and correlating sales activity data from the sampled sales outlets according to the determined distances. The sales activity volume of the product at the plurality of sampled outlets and the estimated sales activity volume of the product at the unsampled outlets are combined to obtain an estimate of sales activity for all the sales outlets. Sales activity of products prescribed by a physician at both the sampled and unsampled outlets can be estimated by correlating sales activity data for the prescribing physician at the sampled outlets according to the distances between the sampled outlets and the unsampled outlets.

U.S. Pat. No. 5,732,401 to Conway illustrates a system for tracking costs of medical procedures by monitoring the movements of personnel, supplies and equipment and processing data on these movements to produce detailed and accurate cost accounting records associated with the particular services rendered. Transponder tags are associated with each person and object for which costs are to be tracked. The detected movements of the tags are combined with scheduling, procedure and cost information to build detailed records of activities and the costs thereof in a manner permitting a wide variety of statistical and other analyses.

U.S. Pat. No. 5,737,539 to Edelson et al. illustrates a prescription creation system for use by professional prescribers at the point of care. The system has a prescription division subsystem permitting creation of a single prescription to be automatically divided into two components for fulfillment of one portion quickly and locally at higher cost and of another portion by remote mail order taking more time but providing a cost saving for a major part of the prescription. The prescription creation system has an ability to access remote source databases for system presentation to the prescriber of relevant, authorized and current drug, drug formulary and patient history information, with dynamic creation of a transient virtual patient record.

In recent years, hospitals and medical facilities have become quite concerned about the unauthorized use/withdrawal of drugs, particularly narcotics, and are demanding systems which allow them to account for such drugs. Hospitals and HMOs have also become concerned about medical practitioners who overprescribe and overutilize expensive and dangerous drugs. To date, the computerized systems in existence have not allowed hospitals and HMOs to gather the information that they need to address these concerns.

SUMMARY OF THE INVENTION

Accordingly, it is an object of the present invention to provide a method and a system for auditing pharmaceutical transactions in a medical care facility.

It is a further object of the present invention to provide a method and a system as above which has great versatility and allows the generation of a wide variety of reports about the distribution and use of drugs within the medical care facility.

It is yet a further object-of the present invention to provide a method and system as above which can be used to identify medical practitioners or users who overprescribe and/or overuse drugs.

It is still a further object of the present invention to provide a method and system as above which can be used to determine whether drugs are being diverted.

The foregoing objects are attained by the drug auditing method and the system of the present invention.

In accordance with the present invention, the drug auditing system comprises an automated drug delivery system for dispensing a plurality of drugs to medical care providers or users, which delivery system has a plurality of drug dispensing stations located throughout the medical care facility and a centralized archive for storing data. Each drug dispensing station includes a console for inputting information about each transaction involving at least one of the drugs and a link for transferring the inputted information to the centralized archive. The system further comprises a processing unit for receiving the transactional information from the centralized archive and for processing it so as to generate at least one report for a defined period of time which detects patterns and abnormalities in distribution and usage of selected ones of the drugs. The processing unit includes a data manager module, a client profile module, a client analyzer module, and a report generator module.

The auditing method of the present invention broadly comprises the steps of: providing an automated drug delivery system for dispensing a plurality of drugs to medical care providers (users); said providing step comprising placing a data source station at each location within the facility where at at least one of said drugs is to be dispensed by a medical care provider; inputting information about each transaction involving at least one of said drugs into a respective data source station whenever one of said drugs is being dispensed; storing said inputted transactional information in a centralized archival database forming part of the drug delivery system; and processing the transactional information in the archival database and generating at least one report for a defined period of time which detects any patterns and abnormalities in the distribution and usage of selected ones of said drugs.

The drug auditing method and system of the present invention were developed because of the need to place controls through auditing on the dispensing of narcotics within an automated drug delivery system.

Other details of the drug auditing method and system of the present invention, as well as other objects and advantages attendant thereto, are set forth in the following detailed description and the accompanying drawings in which like reference numerals depict like elements.

DETAILED DESCRIPTION OF THE PREFERRED EMBODIMENT(S)

As previously discussed, the present invention relates to a method and a system for use in medical care facilities, such as hospitals, to audit the usage of medications and drugs, particularly narcotic drugs. The method and system of the present invention utilize the medical care facility's automated drug delivery system(s) as the source for its data. Most medical care facilities deliver drugs to the patient care floors via this automated drug delivery system(s). These systems distribute drugs much like a bank automated teller machine distributes money to its customers.

Figure 1:
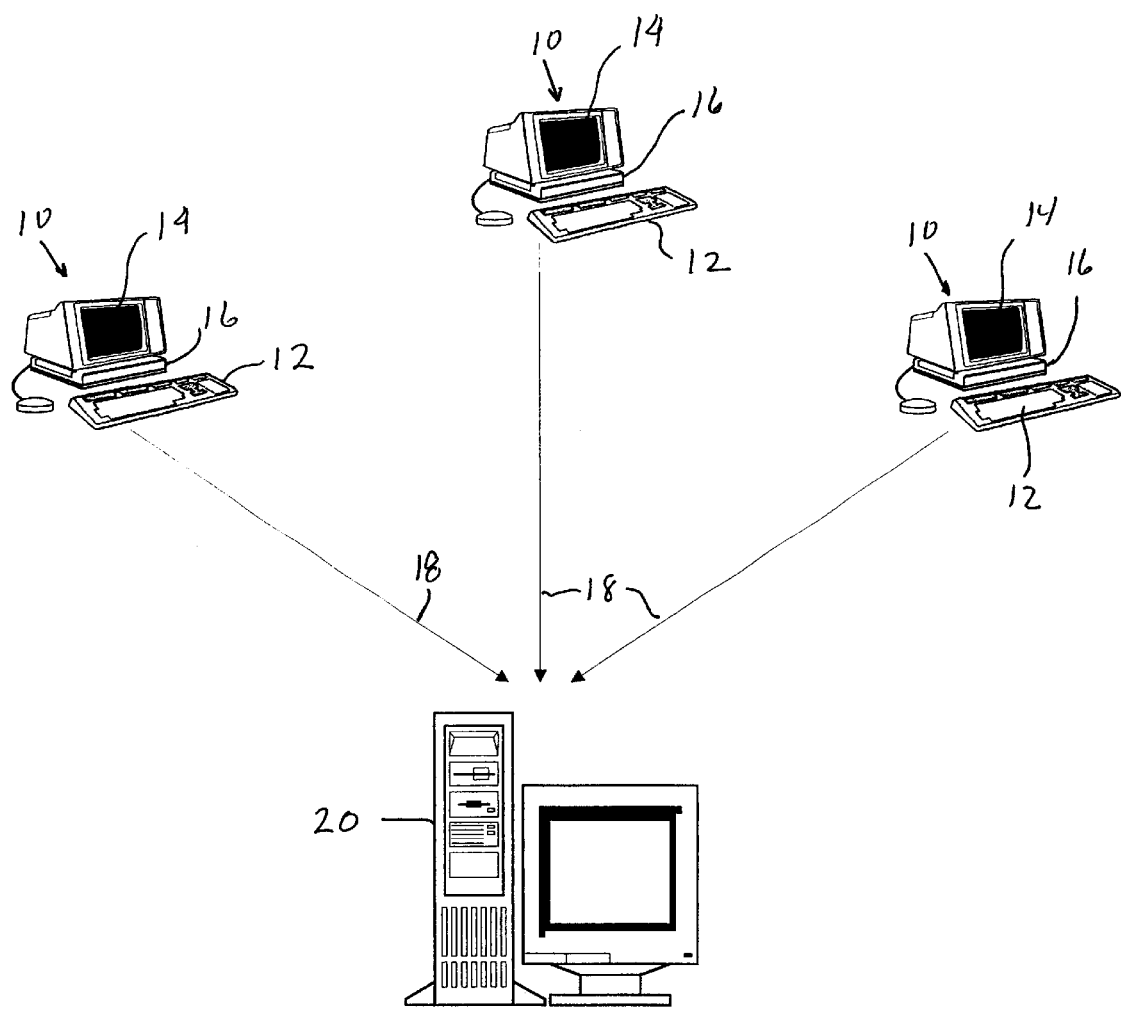
FIG. 1 is a schematic representation of an automated drug delivery system.

Referring now to FIG. 1, a typical automated drug delivery system includes a plurality of stations 10 throughout the medical care facility. At least one station 10 is located in each patient care unit (surgical floor, emergency room, etc.). The station 10 includes a console 12 for entering transactional information, a monitor 14 for displaying the information as it is being entered, and a computer 16 for processing the information being inputted and for authorizing the release of medications and drugs in certain dosages or quantities after the user has been properly identified. Each station 10 is linked via the computer 16 and appropriate data transmission lines 18 to a central computer 20. The central computer 20 stores all transactional information throughout the medical care facility in a database which can then be off-loaded on a periodic basis to external storage medium, i.e., diskette, tape, or CD-Rom.

Automated drug delivery systems create volumes of transactional data every time a medication or drug is vended to a user (medical care provider). The transactional data typically includes the time and date of each transaction, station identification, the name of the medication or drug (med-name), an item number for the medication or drug (med-id), user identification (user id), the quantity or dose dispensed (quantity), the type of transaction (trans-type), the name of the patient (patient-name), and witness identification (witness). The medical care facility may define other information which may be inputted into the station 10 via console 12.

The following transactions typically take place at each station 10. They depict the type of events being processed by users of each station. Representative transaction types are:

INV Transaction=User performing inquiries for inventory purposes;

WTH Transaction=User withdrawing a medication;

OVD Transaction=User overriding the dispensing of a medication;

WAS Transaction=User performing waste of a medication;

CAN Transaction=User canceling a withdrawal; and

DIS Transaction=User finding a discrepancy of inventory.

Throughout a defined period of time, such as a calendar month, the medical care facility gathers the transactional data and aggregates it into a single file within the central computer 20. This data is acquired from the automated drug delivery system described in FIG. 1 via the data acquisition module of the data manager module 24. It is this aggregate data which is processed by the drug auditing system and method of the present invention.

Figure 2:
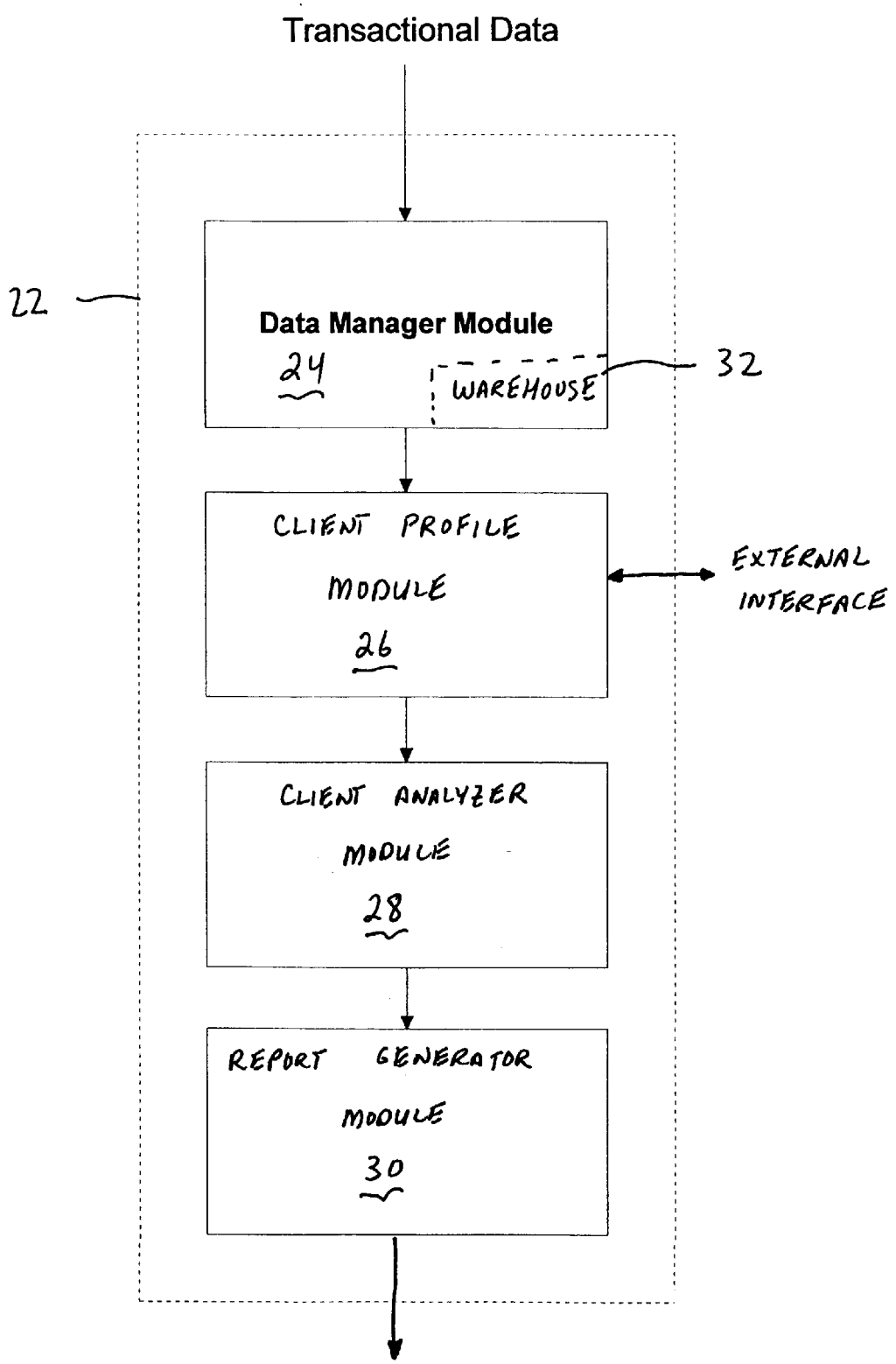
FIG. 2 is a generalized schematic representation of the processing unit used in the auditing system of the present invention to audit the drug delivery system of FIG. 1.

Referring now to FIG. 2, the drug auditing system of the present invention includes a processing unit in the form of a computer 22 which has been programmed to process the aggregate drug transactional data in accordance with the present invention to detect patterns and abnormalities in the distribution and usage of medications or drugs of interest to the medical care facility (the client). The computer 22 may comprise any suitable computer known in the art and may be programmed using any suitable programming language. In accordance with the present invention, the computer 22 is programmed to have a data manager module 24, a client profile module 26, a client analyzer module 28 and a report generator module.

Prior to transferring the aggregate file from the central console 20 to the computer 22, the aggregate file preferably is saved to a storage medium, such as a tape, CD-Rom, or diskette, so as to keep a clean version of the data as well as a vehicle to return the data to the client. Actual transfer of the aggregate file may be effected via the Internet or by hand via tape, diskette or CD-Rom. If transfer is effected via the Internet, the central console 20 and the computer 22 would each have a modem and a telephone line.

Figure 3:
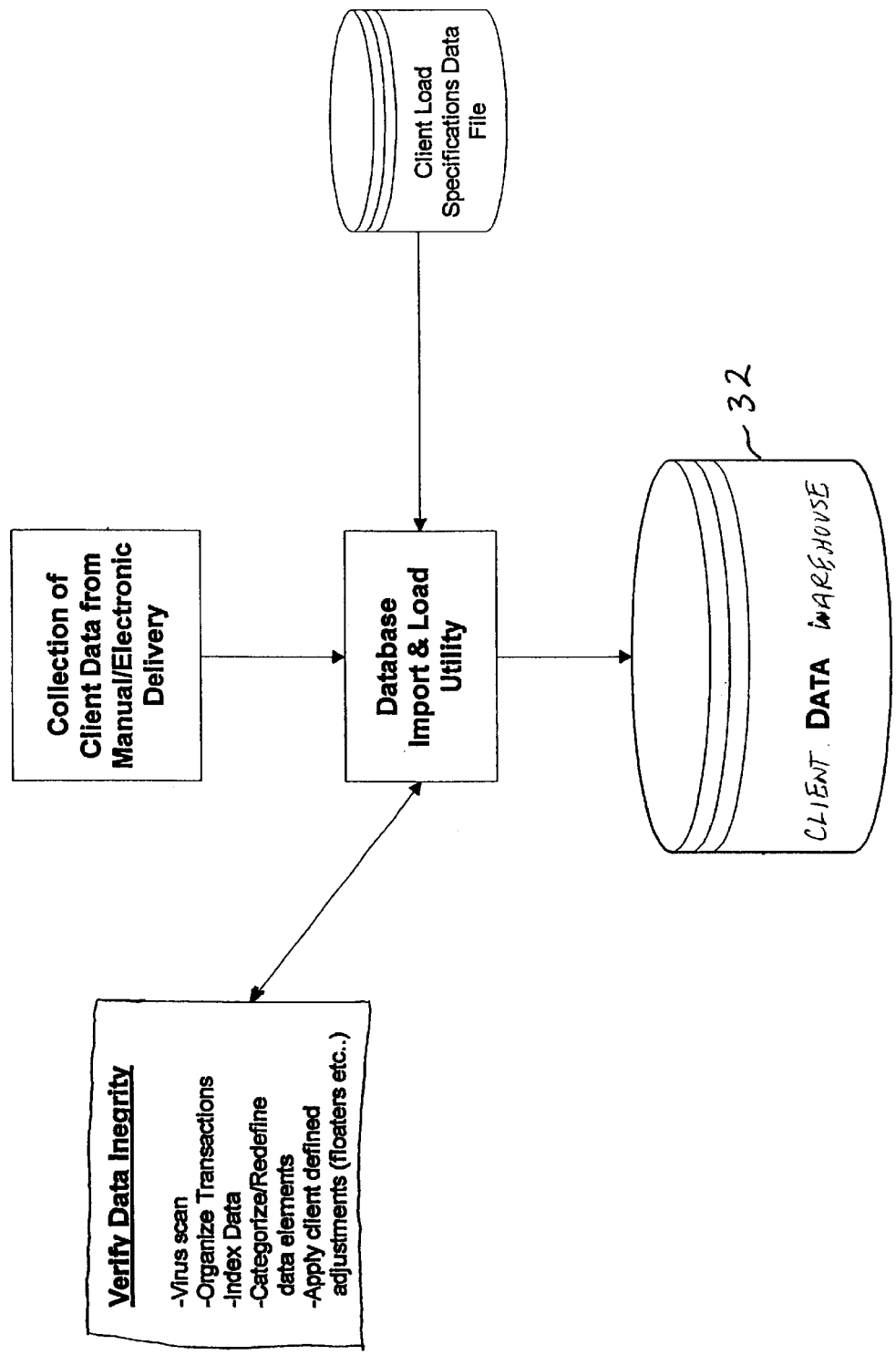
FIG. 3 is a schematic representation of the data manager module of the processing unit of FIG. 2.

FIG. 3 is a schematic representation of the data manager module 24 and the various functions performed therein. As can be seen from this figure, the transmitted data received by the data manager module 24 is subjected to a series of tests to verify data integrity. First, all data is checked for physical data errors. Second, the data is checked for viruses which may corrupt all or parts of the data. Once these low level checks have been completed successfully, the data is then checked for completeness. During this test, the data is checked to see if there are any missing gaps in data (transactions for each day of the defined period of time should be represented). The various tests conducted by the data manager module 24 may be performed using any suitable program known in the art. The data manager module 24 also organizes the transactions, indexes the data, categorize/redefine data elements and adjusts the data as per client defined specifications which are loaded into the data manager module 24.

The data manager module 24 adjusts the transactional information data per specifications defined by the medical care facility by running a series of parameter driven import queries. As used herein the term "query" refers to a pre-defined set of rules (in code) which is executed to derive a specified (pre-determined) outcome. The data adjustment is performed by interrogating each data element of each transaction and first comparing its data structure to that of a predefined mask required for that data element. As used herein, a data mask is a predefined format of how the data should be viewed, i.e., a date is shown as month, date, year. Once all data elements have been parsed for structure compliance, the data manager module 24 creates appended data elements which are calculated/derived data elements required by the client analyzer module 28. The adjusted data elements are used to reclassify or re-organize record sets in subsequent processing.

One adjustment which may be made is to group stations (stat-adj) of "like users" together. This means that the medical care facility must identify which stations 10 in the drug delivery system service the same group of users, i.e. all surgical floor stations must be linked together. This is needed so that all surgical users can be benchmarked against each other.

Another adjustment which can be made to the data is to reclassify special users if specific categories of users have special processing requirements as defined by the medical care facility. An example of this would be a temporary user or floating users.

All data which has been checked and adjusted is then archived to an aggregate data warehouse 32. The warehouse 32 may be formed by storage space within the data manager module 24 or may be an external storage device such as a tape, CD-Rom, or diskette which can be accessed by the data manager module 24. The warehouse 32 typically contains the client's monthly automated drug delivery system transactions archived from previous months of activity. Thus, the warehouse 32 is a cumulative repository which represents a historical snapshot of the automated drug delivery system data and which provides the medical care facility with a platform from which automated drug delivery system information can be obtained via drug auditing and statistical analysis.

The warehouse 32 preferably has a relational data structure based on the data repository of a singular client. The warehouse 32 is segregated into several data sources A1, A2, B1, B2, etc., which are segregated due to diversity of their data type and structure. As used herein, the term "data sources" refers to subsets of the data which have different characteristics (formatted differently). Therefore, they must be identified and stored separately. An example might be a medical care facility which is running two versions of an automated drug delivery system.

The client profile module 26 provides the custom features required by the client for data filtering, exclusion, and external data source entry. The module 26 allows the client analyzer module 28 to provide unlimited flexibility for custom reporting. The module 26 draws the data from the warehouse through data pipes 26A, 26B, and 26C based on the destination query's, i.e. drug audit, transaction audit, and/or detail level audits, required data source. Thereafter, the data being piped from the data sources is aggregated into one naturalized data source within module 26. This means that the data from the data sources take on the same format characteristics. The module 26 then applies the contents of each of the client parameter tables described below against the queries to be executed to further filter the data contained in the data pipes.

In processing the data during this stage, there may be. certain client defined data exclusions. For example, the client may require that certain stations be eliminated from drug control report functions. To accomplish this, the module 26 allows the creation of a table which all report functions use during data source filtering. For example, clients may choose to exclude transactions associated with their narcotics vault. The narcotics vault is a specialized station used internally in the medical care facility pharmacy. Pharmacists withdraw narcotics from this station in order to fill automated drug delivery system stations in the patient care units. Still further, specific users may be excluded. For example, transactions created by pharmacists and pharmacy transactions are sometimes ignored from drug control reports because these users are frequently adjusting medications in the patient care units as a matter of daily operations. If these users were not excluded the statistical results will be skewed. The client may have other custom rules for exclusion of data. All client defined exclusion rules are set up at the time of client definition in the client exclusion table which is stored in module 26.

The client profile module 26 also performs data source filtering. This filtering operation is designed to reduce the size and volume of data to be handled by the drug control queries. The idea is to limit the size and number of data elements required for each query by using a set of client defined tables.

One such client defined table which may be established is the drug audit parameter table (TABLE I) shown in Appendix I attached hereto. In this table, clients predefine categories of drug types, for example, where a specific narcotic (such as morphine) may have many unit-doses defined within the automated drug delivery system by drug item number (med-id). In order to group all the drug items for this narcotic together as one, the client must identify how to link them. Once this is done, the drug audit parameter table drives the data source filtering necessary for the drug audit query. Both controlled and non-controlled drugs may be defined within this table.

Another table which can be assembled is a transaction audit parameter table (TABLE II) such as that shown in Appendix I attached hereto. Here, categories of transaction types to be audited during execution of the transaction audit query are predefined. This table also provides any additional filter limitations to be combined with the filtering of specified transactions.

Yet another table which may be created by this module is a detail report parameter table which defines the data filtering parameters for each of the detail reports associated with the system of the present invention. This table specifies the order of detail report execution and the specific data filtering criteria for each detail report. A sample of a data report parameter table (TABLE III) is shown in Appendix I attached. hereto.

The client profile module 26 is also used to interface external data sources with the client analyzer module 28 which uses the external data sources as additional inputs to the appropriate drug control queries. For example, the client profile module 26 may interface with external payroll information needed to create a payroll interface table which may be used to determine a weighted factor for users based on the number of hours worked during the time period being audited.

Figure 4A:
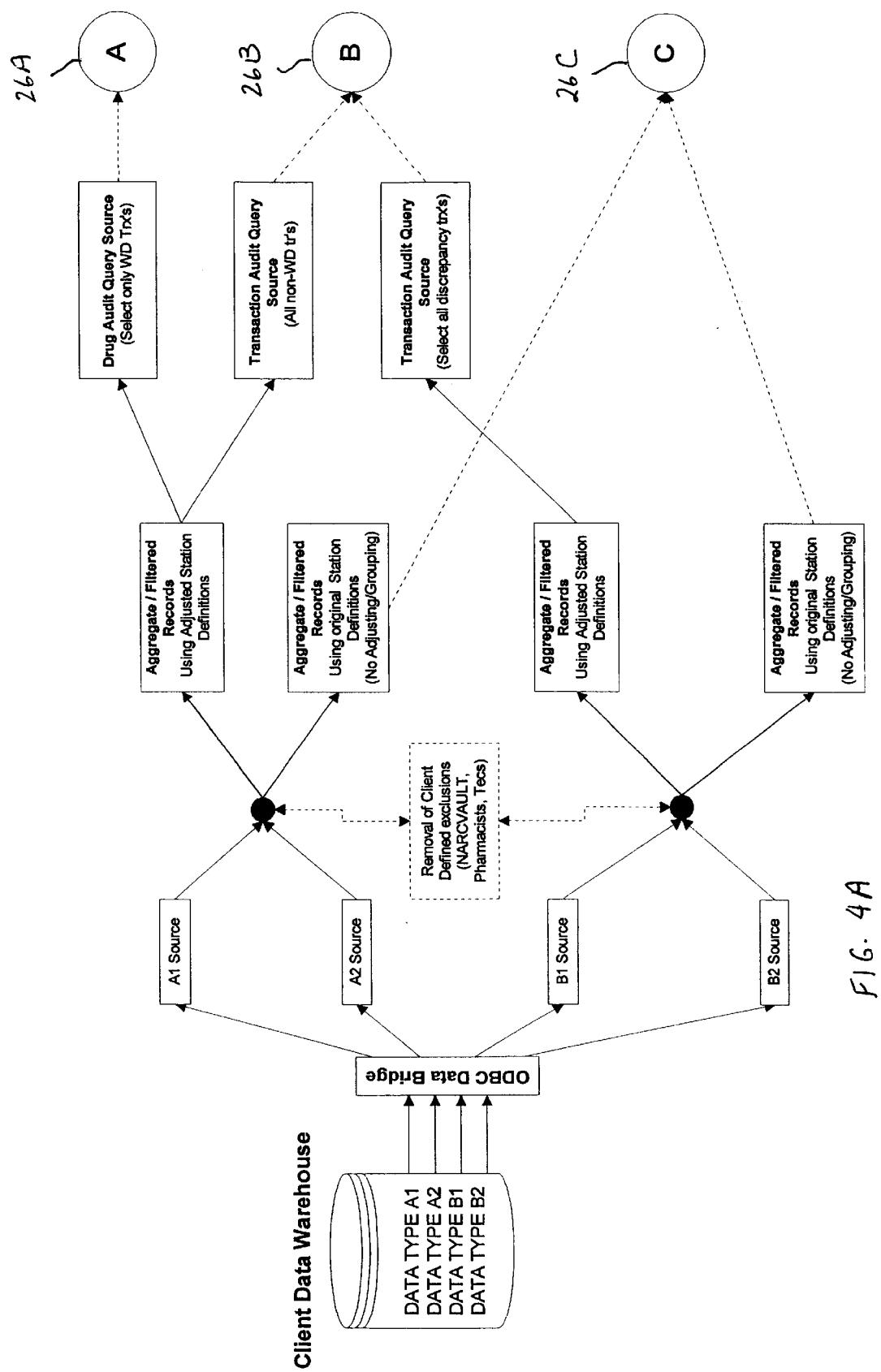
FIGS. 4A, 4B and 5 are flow charts illustrating how drug transactional data is processed.
Figure 4B:
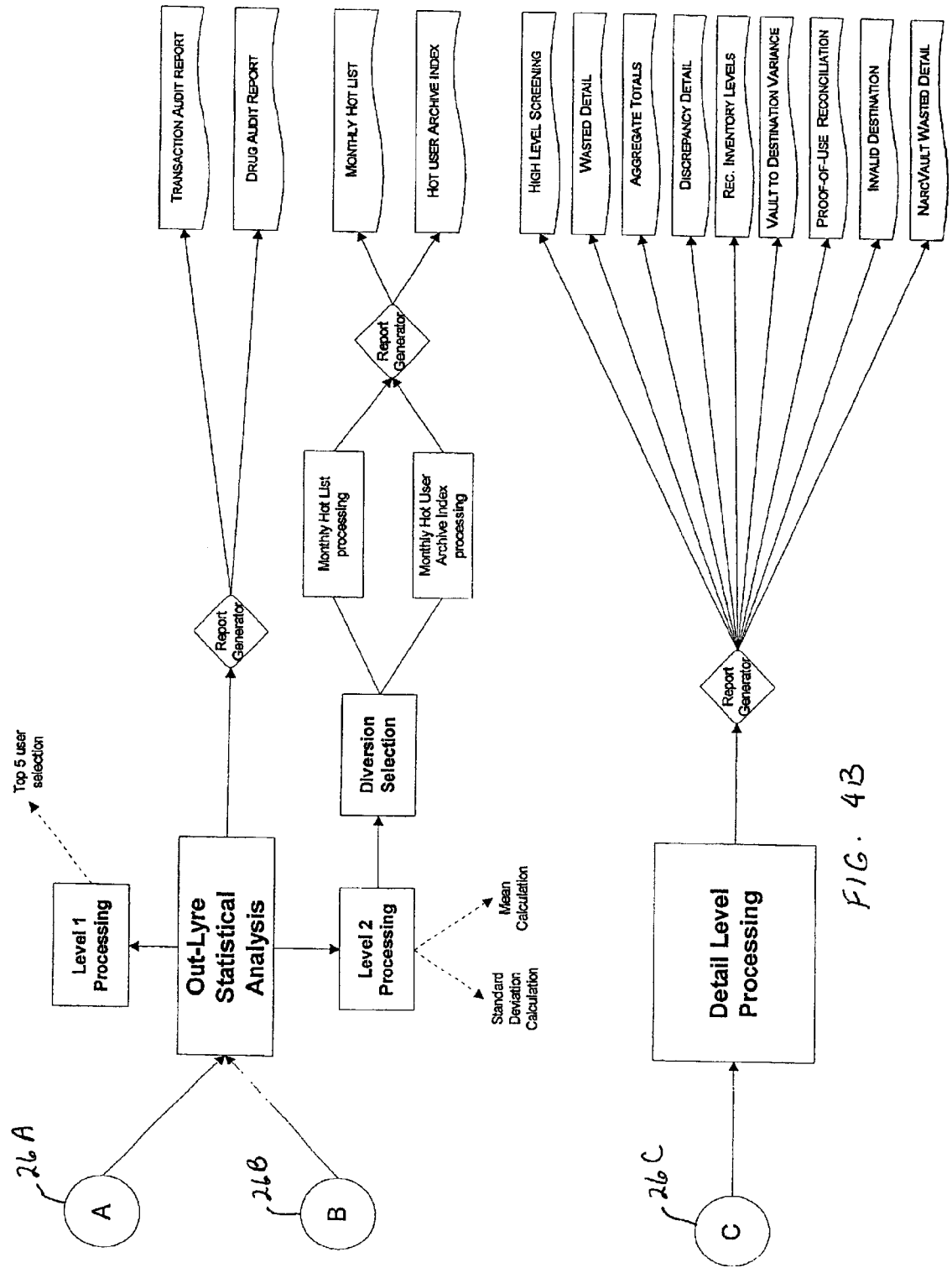
Figure 5:
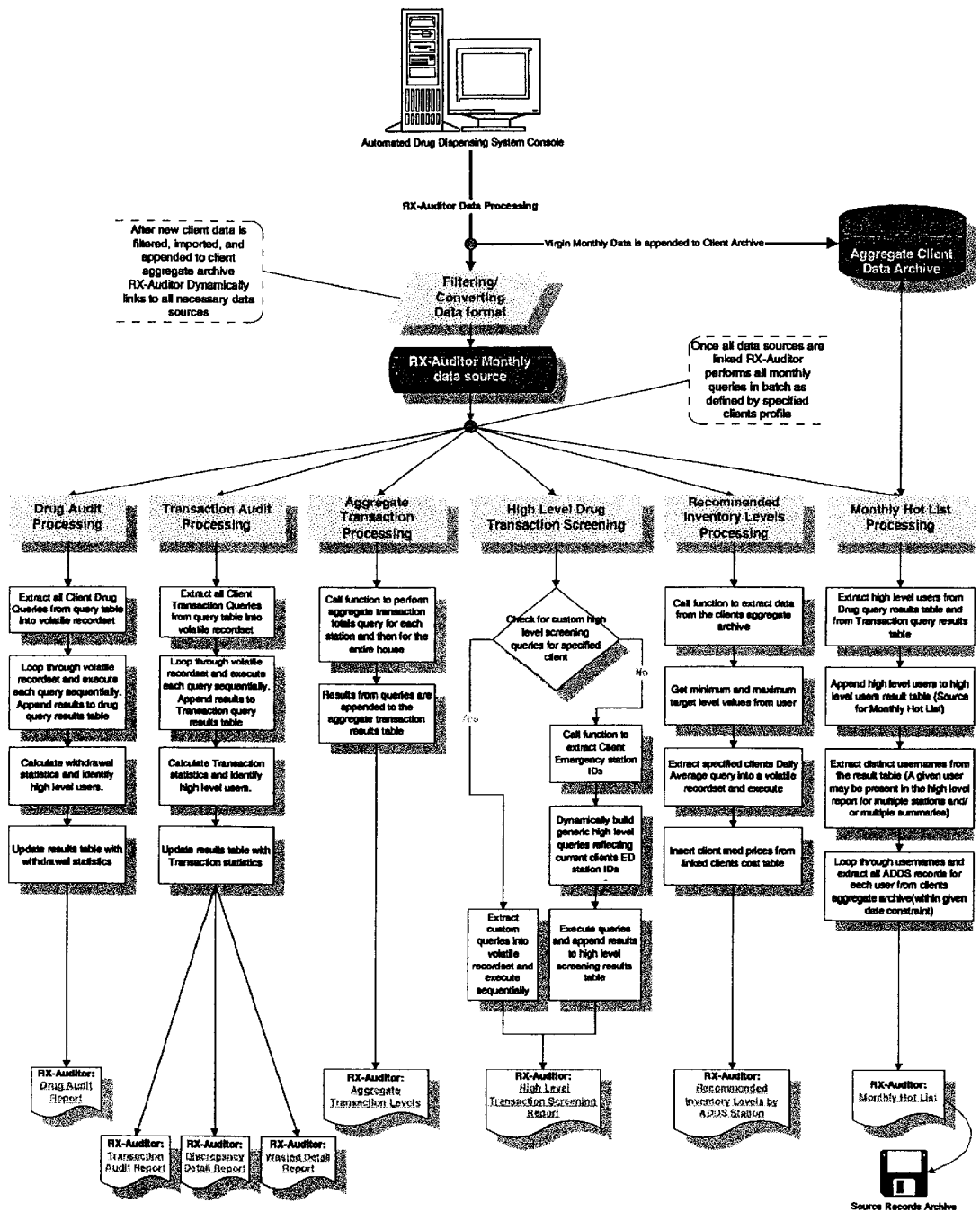

The client analyzer module 28 contains the drug control data analyzer functionality. This module performs all data queries necessary to create the resulting end user reports and employs the concept of benchmarking "like users" of automated drug delivery systems in a medical care facility against each other. This is because in order to detect drug diversion amongst users in an automated drug delivery system environment, there must be a controlled method for developing a base line for the measurement of diversion. FIGS. 4A. 4B and 5 are flow charts showing how the transactional information data is processed to yield a drug audit report, a transaction audit report and the other reports created by the client analyzer module 28.

In order to achieve "like user" benchmarking, the client analyzer module 28 is programmed to group automated drug delivery stations by patient care unit with the same type of service. For example, if a medical care facility has two floors defined as surgical floors, then the automated drug delivery system stations supporting the users of those floors are linked together and analyzed as one station. In this way, all users (practitioners) providing the same type of patient care can be benchmarked against themselves. This provides the client analyzer module 28 with the base line necessary to apply meaningful statistical inferences.

In order to achieve "like drug" type benchmarking, the client analyzer module 28 is programmed to group automated drug delivery system defined drug items (same drug but separate unit/doses) with the same root drug name together. For example, if the client chooses to audit the root drug name of morphine, then the client analyzer module 28 is programmed to link together all drug items defined to the automated drug delivery system with a unit/dose definition associated to morphine. In the case of morphine and many other narcotics, there are several unit/dose strengths (drug items) associated to the root drug name. Therefore, all possible variations of a like drug type (root drug) can be benchmarked together. This provides the client analyzer module 28 with a second base line, which also allows for a more accurate statistical analysis.

The client analyzer module 28 is programmed to control the execution of certain queries needed to generate the desired reports. For example, the module 28 controls the execution of the drug audit query needed to generate a drug audit report. This report requires the module 28 to draw data from the warehouse 32 via the client profile module 26. Data source types are aggregated in the module 28 and the data elements necessary for the drug audit query are selected, namely stat-adj, user, med-name, med-id and quantity. Selecting only withdrawal transactions further filters data for the drug audit query. The client profile module 26 limits the data source by filtering the data source against the drug audit parameter table. Thus, this process only selects withdrawal transactions which match controlled and non-controlled drug entries found within the drug audit parameter table. The query performed by the module 28 totals all withdrawal quantities for the drug(s) being audited. Then data is ordered by med-name, user, station-adj. Once the above detail data is selected and ordered the query will group the data by station-adj, med-name, and user in descending sequence.

Level 1 diversion detection is accomplished by capturing the top five users being benchmarked, for the station being audited, based on the quantity withdrawn for the drug(s) being audited.

Level 2 diversion detection is accomplished by first totaling the quantity withdrawn for the med-name being audited within the station being audited. The number of users for the station being audited is then totaled. The mean average per med-name is obtained by dividing the total withdrawal quantity for the med-name being audited by the total number of users in the station being audited.

The module 28 then calculates the standard deviation of the med-name being audited for the station being audited. Those users which are at least two units of standard deviation above the mean are flagged. Users who are three or more units of standard deviation above the mean are separately identified. Users who are flagged using this standard deviation analysis are targeted and selected as an input to a hot list for the defined period, typically a month.

The client analyzer module 28 performs a level 3, chi squared statistical inference. This involves random sampling of other patient care providers against like patients, determining the percentage of narcotics vs. non-narcotic dispensed by the practitioner in question vs. a like practitioner. This results in a 99.8 confidence level for drug diversion detection. The module 28 also controls the execution of the transaction audit query. This query again draws data from the warehouse via the client profile module 26. Data source types are aggregated and the data elements necessary for the drug audit query are selected, namely station-adj, user, med-name, trans type. The transaction audit query also aggregates the discrepancy transaction data sources. The client profile module 26 limits the data source by filtering the data source against the stored transaction audit parameter table. This process only selects those transactions which match the transaction types defined within the transaction audit parameter table.

The query performed by the module 28 first counts the total number of transactions found in the data source being filtered for each transaction type defined in the transaction audit parameter table. The data is ordered by trans type, user, station adj. Once the above detailed data is selected and ordered, the query groups the data by station adj, trans-type, and user in descending sequence.

Level 1 diversion detection is accomplished by capturing the top five users being benchmarked, for the station being audited, based on the total number of transaction types being audited.

Level 2 diversion detection is accomplished by first totaling the total transaction count of the transaction types being audited within the station being audited. The number of users for the station being audited is then totalled. The mean average count of transactions being audited per trans-type is determined by the module 28 by dividing the total count of transactions being audited by the total number of users in the station being audited. The standard deviation of the trans-type being audited for the station being audited is then calculated by the module 28. Those users who are at least two standard deviation units above the mean are flagged. Users which have been flagged are targeted as level 2 diverters and are selected as an input to the defined period hot list.

The level 3 diversion detection, using a technique similar to that described above, drug audit and transaction audit queries executed by the module 28 are designed to perform station-level and house-wide diversion analysis. The concept of microanalysis (station-level) which is employed therein incorporates the benefits derived from the ability to perform "like user" benchmarking. This enables the client analyzer module 28 to detect drug diversion based on the comparison of users within a patient care unit. However, most automated drug delivery systems allow users to be defined with house-wide security. This means that a subset of the user population has access to all stations across the client hospital. In order to detect diversion amongst these users, the client analyzer module 28 is provided with the capability to execute the drug audit and transaction audit queries with house-wide coverage. This is accomplished by providing instructions to ignore the station-level constraints defined above. During house-wide auditing, the drug and transaction audit queries performed by the module 28 aggregate the user base and benchmark all users against each other.

Many clients have the ability to define temporary and/or floating users within their user base. These types of users are transient users and ordinarily are not assigned to a specific floor or patient care unit for extended periods of time. Normally, these user types are hard to identify as drug diverters. The client analyzer module 28 is provided with the ability to benchmark these users by allowing the client to pre-define these user types within the data manager module 24 so that the data structure to be processed by the module 28 is adjusted accordingly. This allows the drug audit and transaction audit queries used by the module 28 to benchmark these temporary/floating users against themselves.

The monthly hot list previously discussed is executed by the client analyzer module 28 and provides the auditing system and the method of the present invention with the ability to report drug diversion in a concise format. The monthly hot list query performed by the module 28 uses the results database from the drug audit and transaction audit queries as the source for input. The hot list query performed by the module 28 selects station-adj, user, reason for diversion selection, total quantity withdrawn/total transaction count, mean average, and standard deviation.

A hot user archive index may also be created by the client analyzer module 28. This allows the auditing system and the method of the present invention to tie individual drug diverters on the monthly hot list to the supporting detail data necessary to build a case against them. As can be imagined in today's environment, clients require that suspected drug diversion cases have the necessary supporting detail evidence required to support their investigation. This is accomplished by providing the client with a cross-reference report linking the individual to an Excel format file which contains all monthly transactions generated by the individual selected.

The hot user index query performed by the module 28 uses the input from the defined period (monthly) hot list results data base. It selects each hot user by user name and date and pulls all the transactions for that user for the month in question from the warehouse. It then totals the number of transactions selected, creates an Excel file of these transactions, and captures the Excel file size. It also creates a physical link to the Excel file from the physical report.

The client analyzer module 28 also is programmed to execute aggregate transaction totals. This query provides the client with station-level and house-wide aggregate transaction counts for each distinct transaction type generated by the automated drug delivery system. The aggregate transaction totals query performed by the module 28 receives detail level aggregated data sources from the data manager module 24 including discrepancy data. These data sources use non-adjusted data elements which have been filtered for user defined exclusions only by the computer profile module 26. The aggregate transaction total query will select only those transactions which match the month (date constraint) being executed.

High level transaction screening may also be executed by the client analyzer module 28. This query provides the client with a house-wide audit by automated delivery drug system station. This query receives detailed level aggregated data sources from the data manager module 24 for all withdrawal transactions only. The client profile module 26 filters out client defined exclusions which contain non-adjusted data elements. The high-level transaction screening query performed by the module 28 also selects only those withdrawals which meet the data constraint for the month being executed. This query may further filter the data by selecting only narcotics (controlled drugs) where the withdrawal quantity is greater than 2 or where the withdrawal quantity is greater than 3 for stations defined as emergency medicine. Emergency medicine stations may be defined within the client profile module 26. The query reports these detail level transactions by user, patient-name, med-name, date, time, and quantity within station.

The client analyzer module 28 also is programmed to execute a discrepancy transaction detail. This query provides the client with a house-wide audit by automated drug delivery system station. This query receives the discrepancy detail level aggregated data source from the data manager module 24. The client profile module 26 filters out client defined exclusions which contain non-adjusted data elements. The discrepancy transaction screening query performed by the module 28 selects only those discrepancy transactions which meet the data base constraint for the month being executed. This query reports these detail level transactions by user, med-name, Ebc (Expected begin count), Abc (Actual begin count), Diff (Difference between Ebc and Abc), qty, time , date, class (drug classification), trans-type, within station.

A wasted transaction report can also be generated using the client analyzer module 28. This query provides the client with a house-wide audit by automated drug delivery system station. This query receives the detail level aggregated data sources from the data manager module 24 excluding the discrepancy detail data source. The client profile module 26 filters out client defined exclusions which contain non-adjusted data elements. The wasted transaction screening query performed by the module 28 also selects only those wasted transactions which meet the data constraint for the month being executed. This query reports these detail level transactions by user, witness, med-name, amount given (QUANTITY), time, date, within station.

The client analyzer module 28 also is programmed to perform a recommended inventory level by automated drug delivery system station function. This query provides the client with a house-wide audit by automated drug delivery system station. This query receives the detail level aggregated data sources from the data manager module 24 excluding the discrepancy detail data source. The client profile module 26 filters out client defined exclusions which contain non-adjusted data elements. The recommended inventory level query performed by the module 28 selects only those withdrawal transactions which meet the data constraint for the defined time period, such as a fiscal quarter, being executed. The client profile module 26 provides information about client defined unit drug cost which is needed to complete this analysis. This query provides the client with drug utilization for each med-id contained in the station being audited and associates the unit cost to the utilization for each med-id. This query displays the med-id, med-name, unit cost, par (Reorder level), total-withdrawn, total cost, 90-day average, min-target level (minimum number of days), max target level (maximum number of days), avg-cost, within station. It also provides a total of withdrawn, 90-day average, min, max, avg-cost for each station and grand totals for house-wide.

The report generator module 30 is used to generate the various reports created by the client analyzer module 28. Specimens of the type of reports generated by this module are shown in Appendix II attached hereto. The reports include, but are not limited to, a monthly hot list, a hot user archive index, a drug audit report, a transaction audit report, an aggregate transaction totals report, a high level drug transactions screening report, a discrepancy detail report, a wasted transaction detail report, a vault to destination variance report, a proof-of-use reconciliation report, an invalid destination report, a narc-vault wasted transaction detail report, and a recommended inventory level by automated drug delivery system report. The report generator module 30 may be programmed in any desired manner known in the art.

It is apparent that there has been provided in accordance with the present invention a drug auditing system and method which fully satisfies the means, objects and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A computer implemented method for auditing a drug delivery system comprising the steps of:

providing an automated drug delivery system for dispensing a plurality of drugs to medical care providers;

said providing step comprising placing a data source station at each location where at least one of said drugs is to be dispensed by a medical care provider;

inputting information about each transaction involving at least one of said drugs into a respective data source station whenever one of said drugs is being dispensed;

storing said inputted transactional information in a centralized archival database forming part of said drug delivery system; and detecting patterns and abnormalities in distribution and usage of selected ones of said drugs, said detecting step comprising processing said transactional information in said archival database using a programmed processing unit to detect said patterns and abnormalities and generating at least one report for a defined period of time which identifies said detected patterns and abnormalities.

2. The method according to claim 1, wherein said inputting step comprises inputting the identity of said medical care provider, the name of and the item number for each of said drugs being dispensed, the dosage or quantity of each of said drugs being dispensed, station identification, current date and current time.

3. The method according to claim 1, further comprising saving said information in said centralized archival database on an external medium prior to performing said processing step.

4. The method according to claim 1, further comprising:

transferring said transactional information in said centralized archival database to said processing unit; and said processing step comprising testing said transactional information transferred to said processing unit for at least one of physical errors, viruses that may damage data comprising said transactional information, and completeness.

5. A method for auditing a drug delivery system comprising the steps of:

providing an automated drug delivery system for dispensing a plurality of drugs to medical care providers;

said providing step comprising placing a data source station at each location where at least one of said drugs is to be dispensed by a medical care provider;

inputting information about each transaction involving at least one of said drugs into a respective data source station whenever one of said drugs is being dispensed;

storing said inputted transactional information in a centralized archival database forming part of said drug delivery system;

processing said transactional information in said archival database and generating at least one report for a defined period of time which detects patterns and abnormalities in distribution and usage of selected ones of said drugs;

transferring said transactional information in said centralized archival database to a processing unit; and said processing step comprising testing said transactional information transferred to said processing unit for at least one of physical errors, viruses that may damage data comprising said transactional information, and completeness; and said processing step further comprising adjusting said transactional information data in said processing unit so as to group stations of like providers together and to reclassify selected ones of said medical care providers.

6. The method according to claim 4, further comprising:

excluding information from certain stations from the transactional information to be processed by said processing unit to generate said at least one report; and filtering said transactional information to reduce the size and volume of data to be processed by said processing unit.

7. A method for auditing a drug delivery system comprising the steps of:

providing an automated drug delivery system for dispensing a plurality of drugs to medical care providers;

said providing step comprising placing a data source station at each location where at least one of said drugs is to be dispensed by a medical care provider;

inputting information about each transaction involving at least one of said drugs into a respective data source station whenever one of said drugs is being dispensed;

storing said inputted transactional information in a centralized archival database forming part of said drug delivery system;

processing said transactional information in said archival database and generating at least one report for a defined period of time which detects patterns and abnormalities in distribution and usage of selected ones of said drugs;

transferring said transactional information in said centralized archival database to a processing unit; and said processing step comprising testing said transactional information transferred to said processing unit for at least one of physical errors, viruses that may damage data comprising said transactional information, and completeness;

excluding information from certain stations from the transactional information to be processed by said processing unit to generate said at least one report;

filtering said transactional information to reduce the size and volume of data to be processed by said processing unit; and said filtering step comprising defining specific data filtering criteria for each type of report to be generated and storing said criteria in a table.

8. A method for auditing a drug delivery system comprising the steps of:

providing an automated drug delivery system for dispensing a plurality of drugs to medical care providers;

said providing step comprising placing a data source station at each location where at least one of said drugs is to be dispensed by a medical care provider;

inputting information about each transaction involving at least one of said drugs into a respective data source station whenever one of said drugs is being dispensed;

storing said inputted transactional information in a centralized archival database forming part of said drug delivery system;

processing said transactional information in said archival database and generating at least one report for a defined period of time which detects patterns and abnormalities in distribution and usage of selected ones of said drugs;

transferring said transactional information in said centralized archival database to a processing unit; and said processing step comprising testing said transactional information transferred to said processing unit for at least one of physical errors, viruses that may damage data comprising said transactional information, and completeness;

excluding information from certain stations from the transactional information to be processed by said processing unit to generate said at least one report;

filtering said transactional information to reduce the size and volume of data to be processed by said processing unit; and said filtering step comprising creating at least one table defining controlled and non-controlled ones of said drugs and categories of transaction types to be audited during execution of a transaction audit query.

9. The method according to claim 6, further comprising interfacing with external data sources for providing additional information needed as an input to said processing step.

10. A method for auditing a drug delivery system comprising the steps of:

providing an automated drug delivery system for dispensing a plurality of drugs to medical care providers;

said providing step comprising placing a data source station at each location where at least one of said drugs is to be dispensed by a medical care provider;

inputting information about each transaction involving at least one of said drugs into a respective data source station whenever one of said drugs is being dispensed;

storing said inputted transactional information in a centralized archival database forming part of said drug delivery system;

processing said transactional information in said archival database and generating at least one report for a defined period of time which detects patterns and abnormalities in distribution and usage of selected ones of said drugs;

transferring said transactional information in said centralized archival database to a processing unit; and said processing step comprising testing said transactional information transferred to said processing unit for at least one of physical errors, viruses that may damage data comprising said transactional information, and completeness;

excluding information from certain stations from the transactional information to be processed by said processing unit to generate said at least one report;

filtering said transactional information to reduce the size and volume of data to be processed by said processing unit;

interfacing with external data sources for providing additional information needed as an input to said processing step; and said interfacing step comprising interfacing with payroll records for each medical care provider.

11. The method according to claim 1, further comprising:

defining at least one drug to be audited;

said processing step comprising processing said archival database information in said processing unit to gather all records involving withdrawal of said at least one drug from at least one data source station in said system to be audited so as to identify and compile a list of high level providers of said at least one drug from said records.

12. A method for auditing a drug delivery system comprising the steps of:

providing an automated drug delivery system for dispensing a plurality of drugs to medical care providers;

said providing step comprising placing a data source station at each location where at least one of said drugs is to be dispensed by a medical care provider;

inputting information about each transaction involving at least one of said drugs into a respective data source station whenever one of said drugs is being dispensed;

storing said inputted transactional information in a centralized archival database forming part of said drug delivery system;

processing said transactional information in said archival database and generating at least one report for a defined period of time which detects patterns and abnormalities in distribution and usage of selected ones of said drugs;

defining at least one drug to be audited;

said processing step comprising processing said archival database information in a processing unit to gather all records involving withdrawal of said at least one drug from at least one data source station in said system to be audited so as to identify and compile a list of high level providers of said at least one drug from said records; and said processing step further comprising grouping said data source stations by patient care unit with the same type of service.

13. A method for auditing a drug delivery system comprising the steps of:

providing an automated drug delivery system for dispensing a plurality of drugs to medical care providers;

said providing step comprising placing a data source station at each location where at least one of said drugs is to be dispensed by a medical care provider;

inputting information about each transaction involving at least one of said drugs into a respective data source station whenever one of said drugs is being dispensed;

storing said inputted transactional information in a centralized archival database forming part of said drug delivery system;

processing said transactional information in said archival database and generating at least one report for a defined period of time which detects patterns and abnormalities in distribution and usage of selected ones of said drugs;

defining at least one drug to be audited;

said processing step comprising processing said archival database information in a processing unit to gather all records involving withdrawal of said at least one drug from at least one data source station in said system to be audited so as to identify and compile a list of high level providers of said at least one drug from said records; and said processing step further comprising grouping defined drug items with the same root drug name together.

14. The method according to claim 11, wherein said processing step comprises benchmarking said medical care providers of said at least one drug with each other for said at least one data source station.

15. A method for auditing a drug delivery system comprising the steps of:

providing an automated drug delivery system for dispensing a plurality of drugs to medical care providers;

said providing step comprising placing a data source station at each location where at least one of said drugs is to be dispensed by a medical care provider;

inputting information about each transaction involving at least one of said drugs into a respective data source station whenever one of said drugs is being dispensed;

storing said inputted transactional information in a centralized archival database forming part of said drug delivery system;

processing said transactional information in said archival database and generating at least one report for a defined period of time which detects patterns and abnormalities in distribution and usage of selected ones of said drugs;

defining at least one drug to be audited;

said processing step comprising processing said archival database information in a processing unit to gather all records involving withdrawal of said at least one drug from at least one data source station in said system to be audited so as to identify and compile a list of high level providers of said at least one drug from said records;

said processing step further comprising benchmarking said medical care providers of said at least one drug with each other for said at least one data source station; and said benchmarking step comprising totalling the quantity of said at least one drug being audited for said at least one station, totaling the number of medical care providers for said at least one station, and obtaining a mean average for said at least one station by dividing the total withdrawal quantity for said at least one drug by the total number of medical care providers for said at least one station.

16. The method of according to claim 15, wherein said benchmarking further comprises calculating the standard deviation of said at least one drug being audited for said at least one station and flagging those medical care providers which are at least two units of standard deviation above the mean.

17. The method according to claim 15, wherein said report generating step comprises generating a list of medical care providers who have been flagged.

18. The method according to claim 1, further comprising:

said automated drug delivery system including multiple stations within a single operating unit of a medical care facility;

said processing step comprising grouping said transactional information from each of said multiple stations;

said processing step further comprising identifying high level providers of said drugs at said grouped stations.

19. A method for auditing a drug delivery system comprising the steps of:

providing an automated drug delivery system for dispensing a plurality of drugs to medical care providers;

said providing step comprising placing a data source station at each location where at least one of said drugs is to be dispensed by a medical care provider;

inputting information about each transaction involving at least one of said drugs into a respective data source station whenever one of said drugs is being dispensed;

storing said inputted transactional information in a centralized archival database forming part of said drug delivery system;

processing said transactional information in said archival database and generating at least one report for a defined period of time which detects patterns and abnormalities in distribution and usage of selected ones of said drugs;

said automated drug delivery system including multiple stations within a single operating unit of a medical care facility;

said processing step comprising grouping said transactional information from each of said multiple stations;

said processing step further comprising identifying high level providers of said drugs at said grouped stations; and said identifying step comprising benchmarking said providers at said grouped stations against each other.

20. The method according to claim 19, wherein said benchmarking step comprises determining the total quantity of said drugs dispensed at said grouped stations, determining the total number of providers using said grouped stations, and obtaining a mean average for said grouped stations by dividing the total quantity of dispensed drugs by the total number of providers.

21. The method according to claim 16, wherein said benchmarking step further comprises calculating the standard deviation of the total number of said drugs being dispensed for said grouped stations and flagging those providers which are at least two units of standard deviation above the mean.

22. The method according to claim 1, wherein said processing step comprises processing said transactional information in said database so as to generate a report for said defined period of time which identifies all transactions in which drugs being dispensed are wasted and those providers who are wasting said drugs.

23. The method according to claim 1, wherein said automated drug delivery system comprises a plurality of stations and said processing step comprises processing said transactional information in said database so as to generate a report for said defined period of time which identifies said drugs dispensed at a particular one of said stations.

24. A method for auditing a drug delivery system comprising the steps of:
providing an automated drug delivery system for dispensing a plurality of drugs to medical care providers;
said providing step comprising placing a data source station at each location where at least one of said drugs is to be dispensed by a medical care provider;
inputting information about each transaction involving at least one of said drugs into a respective data source station whenever one of said drugs is being dispensed;
storing said inputted transactional information in a centralized archival database forming part of said drug delivery system;
processing said transactional information in said archival database and generating at least one report for a defined period of time which detects patterns and abnormalities in distribution and usage of selected ones of said drugs;
said processing step comprising processing said transactional information in said database so as to generate a report for said defined period of time which identifies discrepancies in drug usage.

25. A method for auditing a drug delivery system comprising the steps of:
providing an automated drug delivery system for dispensing a plurality of drugs to medical care providers;
said providing step comprising placing a data source station at each location where at least one of said drugs is to be dispensed by a medical care provider;
inputting information about each transaction involving at least one of said drugs into a respective data source station whenever one of said drugs is being dispensed;
storing said inputted transactional information in a centralized archival database forming part of said drug delivery system;
processing said transactional information in said archival database and generating at least one report for a defined period of time which detects patterns and abnormalities in distribution and usage of selected ones of said drugs;
said processing comprising auditing said inputted transactional information in said archival database and determining for individual drugs being audited withdrawal quantities greater than two for non-emergency department stations and quantities greater than three for emergency department stations.

26. The method according to claim 23, wherein said individual drug being audited comprises narcotic drugs.

27. A system for auditing drug usage within a medical care facility comprising:
an automated drug delivery system for dispensing a plurality of drugs to medical care providers;
said automated drug delivery system comprising a plurality of drug dispensing stations located throughout said medical care facility and a centralized archive for storing data;
each said drug dispensing station including means for recording information about each transaction involving at least one of said drugs and for transferring said transaction information to said centralized archive; and
means for receiving said transactional information from said centralized archive, for processing said transactional information for a defined period of time to detect patterns and abnormalities in distribution and usage of selected ones of said drugs, and generating at least one report for said defined period of time showing said detected patterns and abnormalities.

28. The system according to claim 27, wherein said receiving and processing means comprises a processing unit having a data manager module, a client profile module, a client analyzer module, and a report generator module.

29. The system according to claim 28, wherein said data manager module comprises means for testing said transactional information received by said processing unit for at least one of physical errors, viruses that may damage data comprising said transactional information, and completeness of said transactional information.

30. A system for auditing drug usage within a medical care facility comprising:
an automated drug delivery system for dispensing a plurality of drugs to medical care providers;
said automated drug delivery system comprising a plurality of drug dispensing stations located throughout said medical care facility and a centralized archive fir storing data;
each said drug dispensing station including means for recording information about each transaction involving at least one of said drugs and for transferring said transaction information to said centralized archive;
means for receiving said transactional information from said centralized archive and for processing it so as to generate at least one report for a defined period of time which detects patterns and abnormalities in distribution and usage of selected ones of said drugs;
said receiving and processing means comprising a processing unit having a data manager module, a client profile module, a client analyzer module, and a report generator module;
said data manager module comprising means for testing said transactional information received by said processing unit for at least one of physical errors viruses that may damage data comprising said transactional information, and completeness of said transactional information; and
said data manager module further comprising means for adjusting said transactional information so as to group like users of said stations and for reclassifying certain categories of users.

31. The system according to claim 29, wherein said data manager module further comprises means for warehousing said transactional information data.

32. The system according to claim 31, wherein said client profile module receives said transactional information data from said warehousing means.

33. The system according to claim 32, wherein said client profile module comprises means for excluding certain data within said transactional information data from further processing.

34. The system according to claim 33, wherein said client profile module further comprises means for filtering said transactional information data so as to limit the size and volume of data to be processed by the client analyzer module.

35. The system according to claim 34, wherein said client profile module comprises means for interfacing with external data sources.

36. A system for auditing drug usage within a medical care facility comprising:
    an automated drug delivery system for dispensing a plurality of drugs to medical care providers;
    said automated drug delivery system comprising a plurality of drug dispensing stations located throughout said medical care facility and a centralized archive for storing data;
    each said drug dispensing station including means for recording information about each transaction involving at least one[]of said drugs and for transferring said transaction information to said centralized archive;
    means for receiving said transactional information from said centralized archive and for processing it so as to generate at least one report for a defined period of time which detects patterns and abnormalities in distribution and usage of selected ones of said drugs;
    said receiving and processing means comprising a processing unit having a data manager module, a client profile module, a client analyzer module, and a report generator module;
    said data manager module comprising means for testing said transactional information received by said processing unit for at least one of physical errors viruses that may damage data comprising said transactional information, and completeness of said transactional information;
    said data manager module further comprising means for warehousing said transactional information data;
    said client profile module receiving said transactional information data from said warehousing means;
    said client profile module comprising means for excluding certain data within said transactional information data from further processing;
    said client profile module further comprising means for filtering said transactional information data so as to limit the size and volume of data to be processed by the client analyzer module; and
    said client analyzer module comprising means for processing said transactional information data received from said client profile module so as to gather all records involving withdrawal of at least one drug being audited from at least one of said stations and to benchmark users of said at least one drug with each other for said at least one station so as to identify those users who exceed a certain threshold level of drug usage.

37. A system for auditing drug usage within a medical care facility comprising:
    an automated drug delivery system for dispensing a plurality of drugs to medical care providers;
    said automated drug delivery system comprising a plurality of drug dispensing stations located throughout said medical care facility and a centralized archive for storing data;
    each said drug dispensing station including means for recording information about each transaction involving at least one of said drugs and for transferring said transaction information to said centralized archive;
    means for receiving said transactional information from said centralized archive and for processing it so as to generate at least one report for a defined period of time which detects patterns and abnormalities in distribution and usage of selected ones of said drugs;
    said receiving and processing means comprising a processing unit having a data manager module, a client profile module, a client analyzer module, and a report generator module;
    said data manager module comprising means for testing said transactional information received by said processing unit for at least one of physical errors viruses that may damage data comprising said transactional information, and completeness of said transactional information;
    said data manager module further comprising means for warehousing said transactional information data;
    said client profile module receiving said transactional information data from said warehousing means;
    said client profile module comprising means for excluding certain data within said transactional information data from further processing;
    said client profile module further comprising means for filtering said transactional information data so as to limit the size and volume of data to be processed by the client analyzer module; and
    said client analyzer module comprising means for processing said transactional information data received from said client profile module so as to gather all records relating to the dispensing of drugs from certain ones of said stations and benchmarking users of said drugs from said stations with each other so as to identify those users who exceed a certain threshold level of drug usage.

38. The system according to claim 34, wherein said client analyzer module comprises means for processing said transactional data received from said client profile module to identify all transactions in which drugs being dispensed are wasted and those users who are wasting said drugs.

39. The system according to claim 34, wherein said client analyzer module comprises means for processing said transactional data received from said client profile module to identify those drugs dispensed at a particular one of said stations.

40. A system for auditing drug usage within a medical care facility comprising:
    an automated drug delivery system for dispensing a plurality of drugs to medical care providers;
    said automated drug delivery system comprising a plurality of drug dispensing stations located throughout said medical care facility and a centralized archive for storing data;
    each said drug dispensing station including means for recording information about each transaction involving at least one of said drugs and for transferring said transaction information to said centralized archive;

means for receiving said transactional information from said centralized archive and for processing it so as to generate at least one report for a defined period of time which detects patterns and abnormalities in distribution and usage of selected ones of said drugs;

said receiving and processing means comprising a processing unit having a data manager module, a client profile module, a client analyzer module, and a report generator module;

said data manager module comprising means for testing said transactional information received by said processing unit for at least one of physical errors viruses that may damage.data comprising said transactional information, and completeness of said transactional information;

said data manager module further comprising means for warehousing said transactional information data;

said client profile module receiving said transactional information data from said warehousing means;

said client profile module comprising means for excluding certain data within said transactional information data from further processing;

said client profile module further comprising means for filtering said transactional information data so as to limit the size and volume of data to be processed by the client analyzer module; and said client analyzer module further comprising means for processing said transactional data received from said client profile module to identify discrepancies in drug usage.

41. A system for auditing drug usage within a medical care facility comprising:

an automated drug delivery system for dispensing a plurality of drugs to medical care providers;

said automated drug delivery system comprising a plurality of drug dispensing stations located throughout said medical care facility and a centralized archive for storing data;

each said drug dispensing station including means for recording information about each transaction involving at least one of said drugs and for transferring said transaction information to said centralized archive;

means for receiving said transactional information from said centralized archive and for processing it so as to generate at least one report for a defined period of time which detects patterns and abnormalities in distribution and usage of selected ones of said drugs;

said receiving and processing means comprising a processing unit having a data manager module, a client profile module, a client analyzer module, and a report generator module;

said data manager module comprising means for testing said transactional information received by said processing unit for at least one of physical errors viruses that may damage data comprising said transactional information, and completeness of said transactional information;

said data manager module further comprising means for warehousing said transactional information data;

said client profile module receiving said transactional information data from said warehousing means;

said client profile module comprising means for excluding certain data within said transactional information data from further processing;

said client profile module further comprising means for filtering said transactional information data so as to limit the size and volume of data to be processed by the client analyzer module; and said client analyzer module further comprising means for processing said transactional data received from said client profile module to identify transactions involving certain drugs where the withdrawal quantities are greater than a certain threshold level.

* * * * *